US012259287B2

(12) United States Patent
Tee et al.

(10) Patent No.: US 12,259,287 B2
(45) Date of Patent: Mar. 25, 2025

(54) LOW HYSTERESIS AND FLEXIBLE PRESSURE SENSITIVE COMPOSITE

(71) Applicant: NATIONAL UNIVERSITY OF SINGAPORE, Singapore (SG)

(72) Inventors: Chee Keong Tee, Singapore (SG); Haicheng Yao, Singapore (SG); Weidong Yang, Singapore (SG); Yu Jun Tan, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 607 days.

(21) Appl. No.: 17/429,071

(22) PCT Filed: Feb. 7, 2020

(86) PCT No.: PCT/SG2020/050061
§ 371 (c)(1),
(2) Date: Aug. 6, 2021

(87) PCT Pub. No.: WO2020/162836
PCT Pub. Date: Aug. 13, 2020

(65) Prior Publication Data
US 2022/0128420 A1    Apr. 28, 2022

(30) Foreign Application Priority Data
Feb. 8, 2019  (SG) .............. 10201901119P

(51) Int. Cl.
*G01L 1/22*       (2006.01)
*B81B 1/00*       (2006.01)
*B81C 1/00*       (2006.01)

(52) U.S. Cl.
CPC ............ *G01L 1/2287* (2013.01); *B81B 1/008* (2013.01); *B81C 1/00111* (2013.01);
(Continued)

(58) Field of Classification Search
CPC .......... G06F 3/016; G06F 2203/04105; G01L 5/226; G01L 1/18; G01L 1/205;
(Continued)

(56) References Cited

U.S. PATENT DOCUMENTS 9,674,949 B1    6/2017  Liu et al.
2014/0104793 A1  4/2014  Park et al.
(Continued)

FOREIGN PATENT DOCUMENTS

CN       108520795 A      9/2018
KR    10-2010-0131593 A    12/2010
(Continued)

OTHER PUBLICATIONS

Pu Nie, High-Performance Piezoresistive Electronic Skin with Bionic Hierarchical Microstructure and Microcracks, 2017 (Year: 2017).*
(Continued)

*Primary Examiner* — John Fitzgerald
*Assistant Examiner* — Truong D Phan
(74) *Attorney, Agent, or Firm* — Volpe Koenig

(57) ABSTRACT

A sensing structure and a method of fabricating a sensing structure for a compressive-type pressure sensor. The method comprises the steps of providing an elastic micropatterned substrate defining a plurality of 3-dimensional microstructures, each microstructure comprising a tip portion pointing away from the substrate in a first direction; forming a conductive film on the elastic micropatterned substrate such that the 3-dimensional microstructures are substantially covered by the conductive film; and forming cracks in the conductive film in areas on 3-dimensional microstructures.

17 Claims, 17 Drawing Sheets

(52) U.S. Cl.
CPC .............. *B81B 2201/0264* (2013.01); *B81B 2203/0361* (2013.01); *B81B 2203/04* (2013.01)

(58) Field of Classification Search
CPC ....... G01L 1/2287; H01H 13/85; B81B 1/008;
B81B 2201/0264; B81B 2203/0361;
B81B 2203/04; B81B 3/0072; B81C
1/00111; A61B 5/0285; B32B 2037/266;
B32B 2309/12
See application file for complete search history.

(56) References Cited

U.S. PATENT DOCUMENTS

| | | |
|---|---|---|
| 2016/0349134 A1 | 12/2016 | Jeon |
| 2018/0033520 A1 | 2/2018 | Yoshida et al. |
| 2018/0068768 A1 | 3/2018 | Kim et al. |

FOREIGN PATENT DOCUMENTS

| | | | |
|---|---|---|---|
| KR | 10-2017-0124828 A | 11/2017 | |
| WO | WO-2017091151 A1 * | 6/2017 | ............. G01L 1/205 |

OTHER PUBLICATIONS

Tee, B. C. K. & Ouyang, J. Soft Electronically Functional Polymeric Composite Materials for a Flexible and Stretchable Digital Future. Adv. Mater. 0, 1802560 (2018).
Kim, D.-H. et al. Epidermal Electronics. Science (80-. ). 333, 838 LP-843 (2011).
Huang, X. et al. A differential dielectric affinity glucose sensor. Lab Chip 14, 294-301 (2014).
Kim, S. J. et al. Stretchable and Transparent Biointerface Using Cell-Sheet-Graphene Hybrid for Electrophysiology and Therapy of Skeletal Muscle. Adv. Funct. Mater. 26, 3207-3217 (2016).
Wang, Y. et al. Wearable and highly sensitive graphene strain sensors for human motion monitoring. Adv. Funct. Mater. 24, 4666 4670 (2014).
Choong, C. L. et al. Highly Stretchable Resistive Pressure Sensors Using a Conductive Elastomeric Composite on a Micropyramid Array. Adv. Mater. 26, 3451-3458 (2014).
Webb, R. C. et al. Ultrathin conformal devices for precise and continuous thermal characterization of human skin. Nat. Mater. 12, 938-944 (2013).
Son, D. et al. Multifunctional wearable devices for diagnosis and therapy of movement disorders. Nat. Nanotechnol. 9, 397-404 (2014).
Ko, H. C. et al. A hemispherical electronic eye camera based on compressible silicon optoelectronics. Nature 454, 748-753 (2008).
Song, Y. M. et al. Digital cameras with designs inspired by the arthropod eye. Nature 497, 95-99 (2013).
Rus, D. & Tolley, M. T. Design, fabrication and control of soft robots Terms of Use Design, fabrication and control of soft robots. Nature 521, 467-475 (2015).
Lu, N. & Kim, D.-H. Flexible and Stretchable Electronics Paving the Way for Soft Robotics. Soft Robot. 1, 53-62 (2014).
Tee, B. C. K. et al. A skin-inspired organic digital mechanoreceptor. Science (80-. ). 350, 313-316 (2015).
Lee, S. K. et al. Stretchable Graphene Transistors with Printed Dielectrics and Gate Electrodes. Nano Lett. 11, 4642-4646 (2011).
Yeo, W.-H. H. et al. Multifunctional Epidermal Electronics Printed Directly Onto the Skin. Adv. Mater. 25, 2773-2778 (2013).
Lim, S. et al. Transparent and stretchable interactive human machine interface based on patterned graphene heterostructures. Adv. Funct. Mater. 25, 375-383 (2015).
Xu, S. et al. Stretchable batteries with self-similar serpentine interconnects and integrated wireless recharging systems. Nat. Commun. 4, 1543-1548 (2013).

Lu, N., Lu, C., Yang, S. & Rogers, J. Highly sensitive skin-mountable strain gauges based entirely on elastomers. Adv. Funct. Mater. 22, 4044-4050 (2012).
Xu, S. et al. Assembly of micro/nanomaterials into complex, three-dimensional architectures by compressive buckling. Science (80-. ). 347, 154-159 (2015).
Matsuhisa, N. et al. Printable elastic conductors with a high conductivity for electronic textile applications. Nat. Commun. 6, 7461 (2015).
Kaltenbrunner, M. et al. An ultra-lightweight design for imperceptible plastic electronics. Nature 499, 458-463 (2013).
Park, S., Vosguerichian, M. & Bao, Z. A review of fabrication and applications of carbon nanotube film-based flexible electronics. Nanoscale 5, 1726-1727 (2013).
Zhu, Y., Xu, F., Wang, X. & au, Y. Wavy ribbons of carbon nanotubes for stretchable conductors. Adv. Funct. Mater. 22,1279-1283 (2012).
Lee, P. et al. Highly stretchable or transparent conductor fabrication by a hierarchical multiscale hybrid nanocomposite. Adv. Funct. Mater. 5671-5678 (2014). doi:10.1002/adfm.201400972.
Xu, F. & au, Y. Highly Conductive and Stretchable Silver Nanowire Conductors. Adv. Mater. 24,5117-5122 (2012).
Liang, J. et al. Silver Nanowire Percolation Network Soldered with Graphene Oxide at Room Temperature and Its Application for Fully Stretchable Polymer Light-Emitting Diodes. ACS Nano 8, 1590-1600 (2014).
Akter, T. & Kim, W. S. Reversibly Stretchable Transparent Conductive Coatings of Spray-Deposited Silver Nanowires. ACS Appl. Mater. Interfaces 4, 1855-1859 (2012).
Perelaer, J. et al. Printed electronics: the challenges involved in printing devices, interconnects, and contacts based on inorganic materials. J. Mater. Chem. 20,8446 (2010).
Jang, K.-I. I. et al. Soft network composite materials with deterministic and bio-inspired designs. Nat. Commun. 6, 1-11 (2015).
Bae, H. J. et al. Biomimetic Microfingerprints for Anti-Counterfeiting Strategies. Adv. Mater. 27,2083-2089 (2015).
Sun, Y., Choi, W. M., Jiang, H., Huang, Y. Y. & Rogers, J. A. Controlled buckling of semiconductor nanoribbons for stretchable electronics. Nat. Nanotechnol. 1,201-207 (2006).
Cao, G. & Chen, X. Buckling of single-walled carbon nanotubes upon bending: Molecular dynamics simulations and finite element method. Phys. Rev. B—Condens. Matter Mater. Phys. 73,1-10 (2006).
Wang, B., Bao, S., Vinnikova, S., Ghanta, P. & Wang, S. Buckling analysis in stretchable electronics. npj Flex. Electron. 1,5 (2017).
Lamoureux, A. et al. Dynamic kirigami structures for integrated solar tracking. Nat. Commun. 6,1-6 (2015).
Silverberg, J. L. et al. Origami structures with a critical transition to bistability arising from hidden degrees of freedom. Nat. Mater. 14,389-393 (2015).
Carlson, H. Spring manufacturing handbook. (M. Dekker, 1982).
Pineda, F., Bottausci, F., Icard, B., Malaquin, L. & Fouillet, Y. Using electrofluidic devices as hyper-elastic strain sensors: Experimental and theoretical analysis. Microelectron. Eng. 144,27-31 (2015).
Shang, Y. et al. Super-Stretchable Spring-Like Carbon Nanotube Ropes. Adv. Mater. 24, 2896-2900 (2012).
Hyun, D. C. et al. Ordered Zigzag Stripes of Polymer Gel/Metal Nanoparticle Composites for Highly Stretchable Conductive Electrodes. Adv. Mater. 23,2946-2950 (2011).
Sekitani, T. et al. A Rubberlike Stretchable Active Matrix Using Elastic Conductors. Science (80-. ). 321,1468-1472 (2008).
Chen, Z. et al. Three-dimensional flexible and conductive interconnected graphene networks grown by chemical vapour deposition. Nat. Mater. 10,424-428 (2011).
Matsuhisa, N. et al. Printable elastic conductors by in situ formation of silver nanoparticles from silver flakes. Nat. Mater. 16,834-840 (2017).
Extended Search Report issued in corresponding European Patent Application No. 20751862.2 on Mar. 2, 2022, consisting of 14 pp.
Pu Nie et al. "High-Performance Piezoresistie Electronic Skin with Bionic Hierarchical Microstructure and Microcracks" ACS Appl. Mater. Interfaces 2017,9, pp. 14911-14919.

(56) References Cited

OTHER PUBLICATIONS

International Search Report issued on May 2, 2024 in corresponding Singaporean Patent Application No. 11202108467Y, consisting of 4 pp.
Written Opinion issued on Jun. 2, 2024 in corresponding Singaporean Patent Application No. 11202108467Y, consisting of 7 pp.
Cheng, W. et al., Flexible Pressure Sensor with High Sensitivity and Low Hysteresis Based on a Hierarchically Microstructured Electrode. IEEE Electron Device Letters, Dec. 18, 2017, vol. 39, No. 2, pp. 288-291.

* cited by examiner providing an elastic micropatterned substrate defining a plurality of 3-dimensional microstructures, each microstructure comprising a tip portion pointing away from the substrate in a first direction
↘ 2002 forming a conductive film on the elastic micropatterned substrate such that the 3-dimensional microstructures are substantially covered by the conductive film
↘ 2004 forming cracks in the conductive film in areas on 3-dimensional microstructures
↘ 2006
↘ 2000

Figure 20

LOW HYSTERESIS AND FLEXIBLE PRESSURE SENSITIVE COMPOSITE

CROSS REFERENCE TO RELATED APPLICATIONS

This application is a national stage entry of International Patent Application No. PCT/SG2019/050061 filed on Feb. 7, 2020 based on Singapore patent application Ser. No. 10/201, 901119P filed Feb. 8, 2019, which applications are incorporated by reference herein as fully set forth.

FIELD OF INVENTION

The present invention relates broadly to compressive-type sensors, sensing structures for a compressive-type pressure sensor, methods of fabricating a sensing structure for a compressive-type pressure sensor, and methods of fabricating a compressive-type pressure sensor.

BACKGROUND

Any mention and/or discussion of prior art throughout the specification should not be considered, in any way, as an admission that this prior art is well known or forms part of common general knowledge in the field.

Kang et al. [7] developed a crack-based strain sensor by sputtering Pt on a plain polymeric film. When stretching is applied, parallel cracks are formed on the surface of the deposited Pt layer, which increases the resistance of the strain sensor. The resistance also decreases when the strain is released. However, the sensors described in Kang et al. can only be used to detect tensile strains.

Embodiments of the present invention seek to address at least one of the above problems.

SUMMARY

In accordance with a first aspect of the present invention there is provided a sensing structure for a compressive-type pressure sensor, the sensing structure comprising:

an elastic micropatterned substrate defining a plurality of 3-dimensional microstructures, each microstructure comprising a tip portion pointing away from the substrate in a first direction; and a conductive film on the elastic micropatterned substrate such that the 3-dimensional microstructures are substantially covered by the conductive film, wherein the conductive film comprises cracks in areas on 3-dimensional microstructures.

In accordance with a second aspect of the present invention, there is provided a compressive pressure sensor exhibiting a ratio of peak sensitivity to electrical hysteresis of more than about 1E9 $\Omega Pa^{-1} \cdot \%^{-1}$ In accordance with a third aspect of the present invention there is provided a method of fabricating a sensing structure for a compressive-type pressure sensor, the method comprising the steps of:

providing an elastic micropatterned substrate defining a plurality of 3-dimensional microstructures, each microstructure comprising a tip portion pointing away from the substrate in a first direction;

forming a conductive film on the elastic micropatterned substrate such that the 3-dimensional microstructures are substantially covered by the conductive film; and forming cracks in the conductive film in areas on 3-dimensional microstructures.

BRIEF DESCRIPTION OF THE DRAWINGS

Embodiments of the invention will be better understood and readily apparent to one of ordinary skill in the art from the following written description, by way of example only, and in conjunction with the drawings, in which:

FIG. 20 shows a flow-chart 2000 illustrating a method of fabricating a sensing structure for a compressive-type pressure sensor.

DETAILED DESCRIPTION

Embodiments of the present invention can provide a piezo-resistive tactile sensor, which is also referred to herein as TRACE (Tactile Resistive Annularly Cracked E-skin) according to example embodiments, by designing nano-scaled metallic regular annular cracks on a polymeric micro-structured array. Tactile sensors according to example embodiment can advantageously achieve a high sensitivity (more than $10^7$ ohm/kPa) in pressure sensing. Tactile sensors according to example embodiments are advantageously also highly sensitive over a wide pressure range, which is a property not demonstrated by current tactile sensors. In addition, due to the ultra-thin metallic coating used in example embodiments, the sensor shows low hysteresis (2.37%) where the changes of the electrical signals are advantageously independent of the direction of pressure change. Various organic or inorganic thin conductive materials can be used on the polymeric micro-structured arrays according to various embodiments of the present invention, and good testing results were obtained. The facile fabrication method according to example embodiments advantageously enables a low-cost and large-area fabrication of the sensor. TRACE sensor according to example embodiments can be used to trace the arterial pulse. A pulse wave velocity (PWV) of 11 m/s was attained from the carotid artery to radial artery from measurements using an example embodiment, which is comparable to the standard measurement result. By designing the flexible electrodes with multiple channels on a TRACE sensor according to an example embodiment, the localized PWV was traceable only at the radial artery for the first time (~0.6 m/s), to the best of the inventors' knowledge. These excellent performance capabilities make TRACE sensors according to example embodiments of the present invention promising in numerous e-skin applications, e.g. smart home devices, health monitoring system and robotics.

According to example embodiments of the present invention, a technique to create regular cracks on a 3D surface is provided, which advantageously results in the ability to sense both in plane and out of plane forces.

Sensors with a patterned 3D microstructure according to example embodiments have superior sensitivity compared to the planar sensor structures. Designable cracks on 3D microstructure for the detection of compressive tactile information in a wide range according to example embodiments is crucial for considerable sensory applications.

Figure 1:
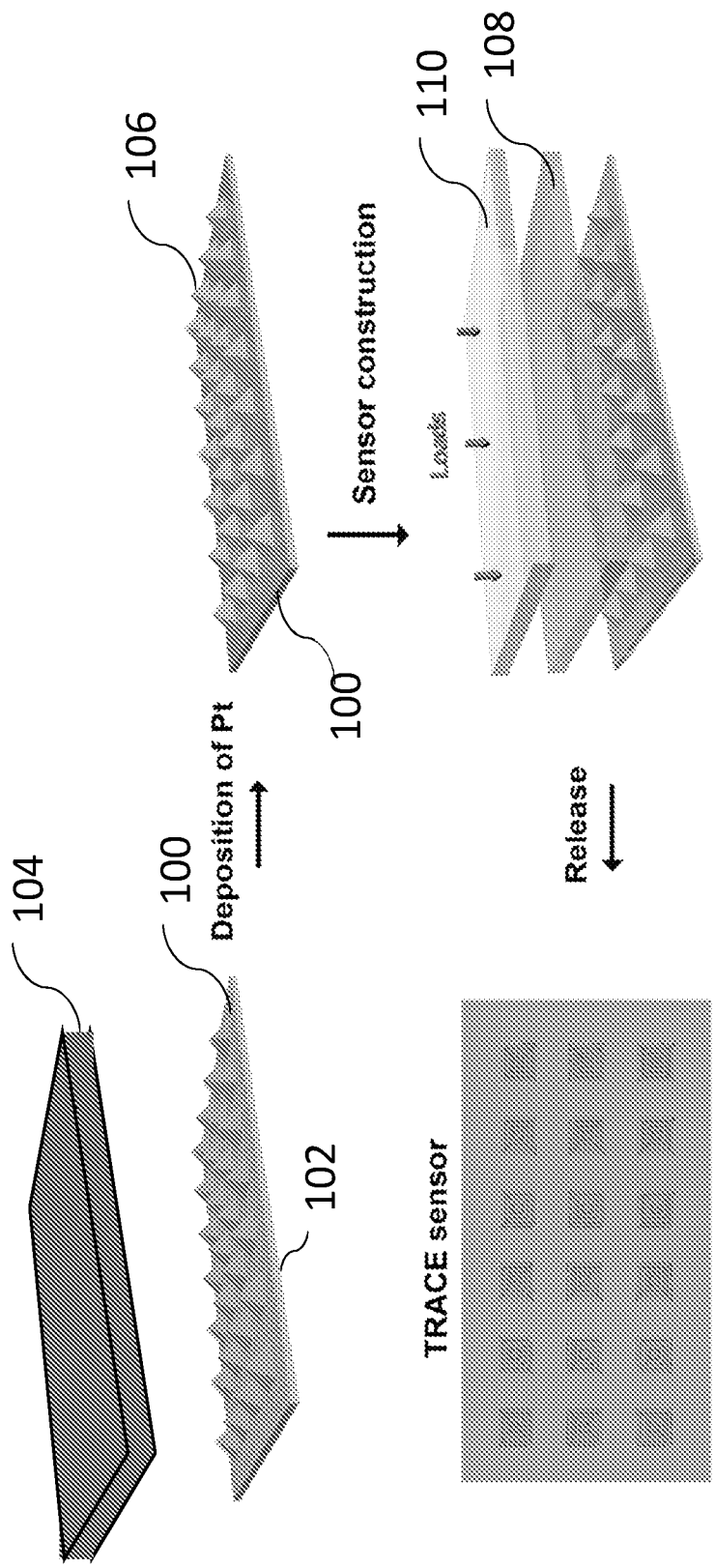
FIG. 1 shows schematic drawings illustrating a method of fabricating a sensing structure, according to an example embodiment.
Figures 2A, 2B:
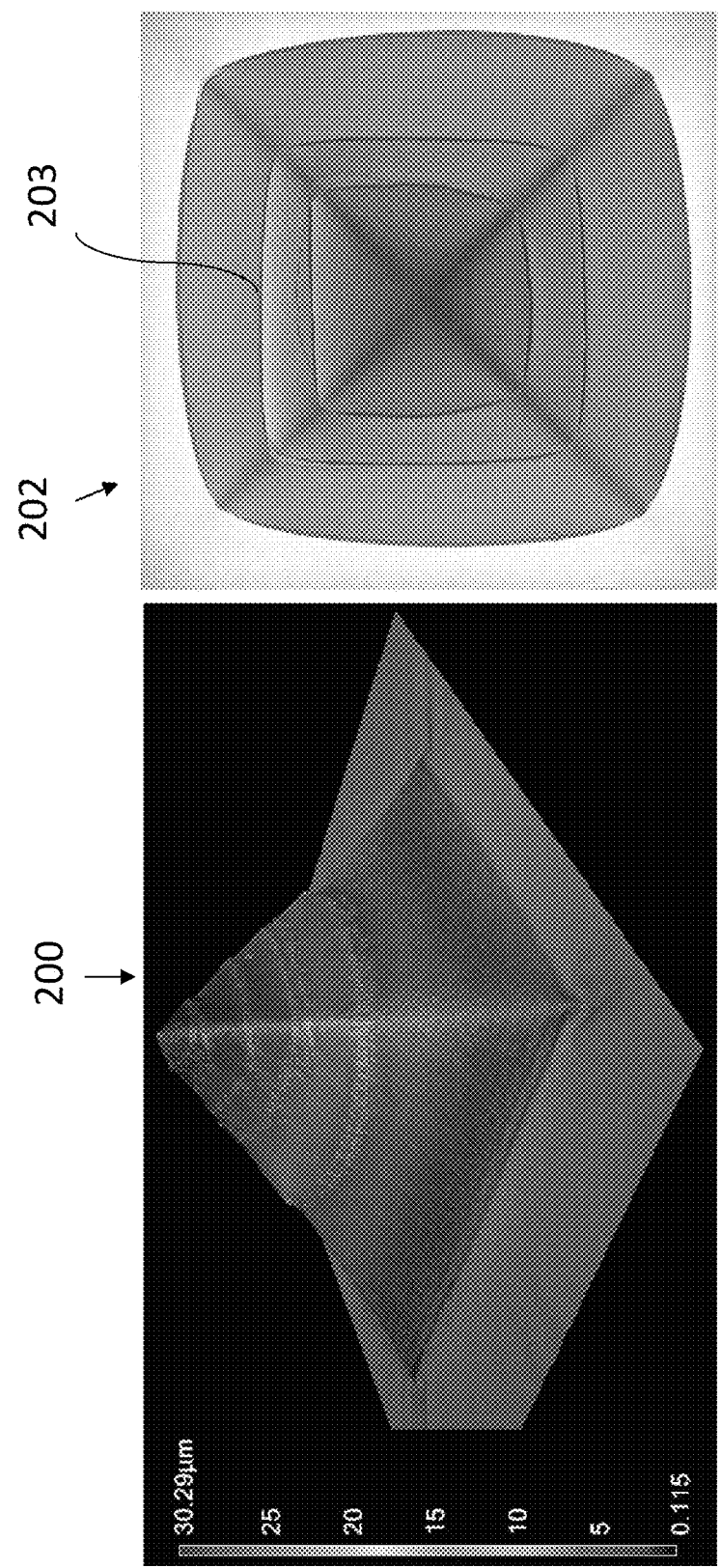
FIG. 2A shows a microscope image of a single 3-dimensional microstructure covered with a conductive film with annular cracks, according to an example embodiment.
FIG. 2B shows ab SEM image of a single 3-dimensional microstructure covered with a conductive film with annular cracks, according to an example embodiment.

Fabrication Method According to an Example Embodiment:

The fabrication flow of TRACE sensor according to an example embodiment comprises, generally, of three major steps (see FIG. 1). First, micropatterned (here micropyramidal in this embodiment by way of example, not limitation) elastomer 100 is cast on a substrate 102 (such as, but not limited to, Si or PET) by using, by way of example, not limitation, a Si mould 104 with the inverse micropyramidal pattern. After peeling off the micropatterned elastomer 100 from the mould 104, the micropatterned elastomer 100 is surface treated and, in this embodiment by way of example, not limitation) platinum (Pt) 106 is sputtered onto the micropatterned surface of the elastomer 100 to form a thin conductive layer (~30 nm). Then, load 107 is applied on the Pt-coated elastomer 106/100 while cushioning with a thin layer 108 of soft material between a rigid substrate 110 and the Pt-coated elastomer 106/100 supported, for example, on a rigid base (not shown) for regular cracks generation. The soft material layer 108 was found to advantageously prevent the cracks from initiating from the tip of the pyramids. Cracks on the tip may limit the sensor response to sudden drop in resistance when pressure increases, instead of the preferable gradual resistance change with pressure. Also, the soft material layer 108 cushioning was found to advantageously distribute the applied load uniformly over the whole surface of the micropyramids for the generation of annular cracks. Images 200, 202 in FIGS. 2A and 2B show laser microscope and SEM images, respectively, of an individual micropyramid of a TRACE sensor according to an example embodiment, with the regular peripheral cracks e.g. 203 clearly visible, as well as the absence of cracks at the tip. The elastomer layer with the microstructures 106/100 remains adhered to the Si/PET/any other substrate 102 in preferred example embodiments.

Figures 3A, 3B:
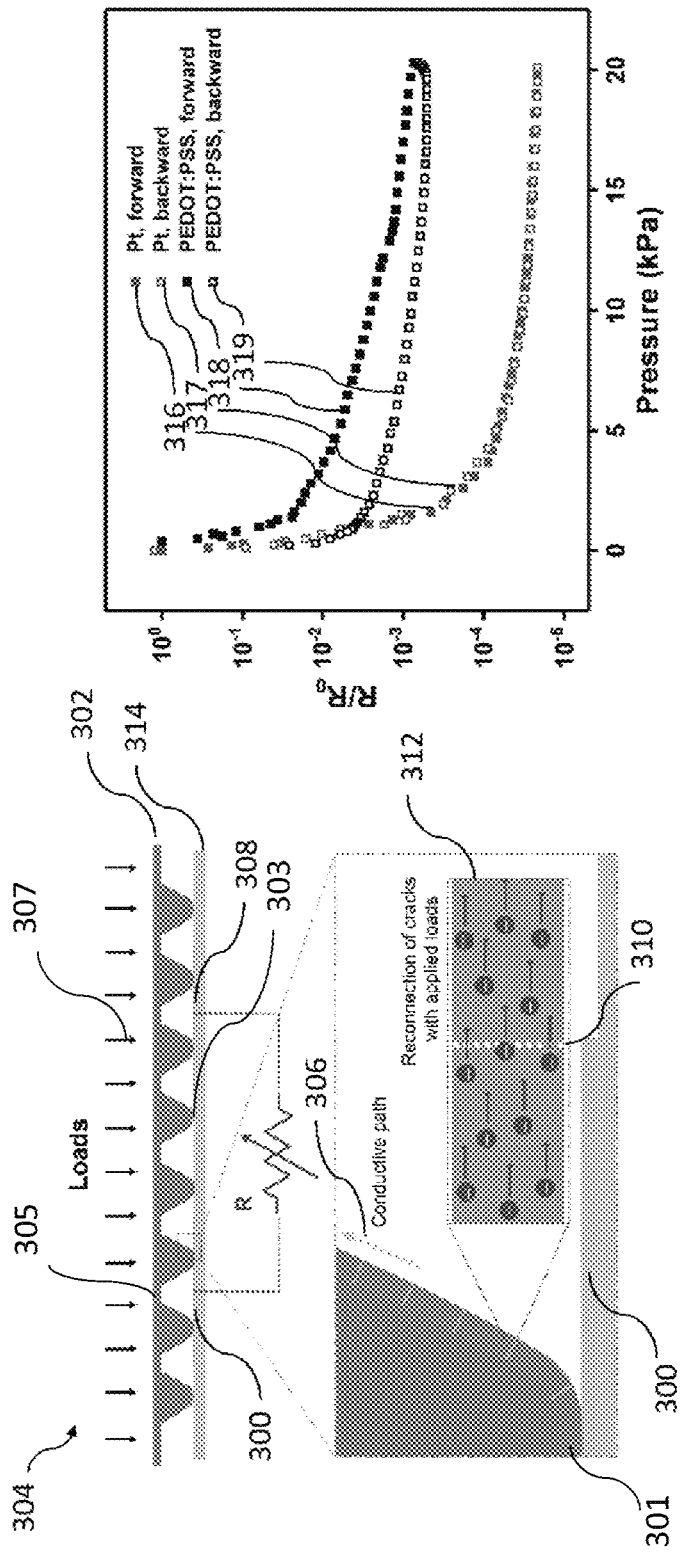
FIG. 3A shows a schematic drawing illustrating an analytical model of the conductive path during loading of a sensor according to an example embodiment.
FIG. 3B shows a graph illustrating pressure-induced electrical performance of a sensor according to an example embodiment, compared with a traditional PEDOT:PSS coated micropyramids sensor.

Results and Discussion of Example Embodiments:

With reference to FIG. 3A, to obtain the resistive pressure response, patterned electrodes e.g. 300 are assembled on the Pt side of micropatterned Pt/elastomer structure 302 with tip portions 301, 303 pointing away from a substrate 305 of a TRACE sensor 304 in a first direction 307, according to an example embodiment. When pressure is applied on the sensor 304, conductive paths e.g. 306 can be generated from one electrode e.g. 300 to the other e.g. 308 through the reconnected cracks e.g. 310 of Pt layer 312. According to example embodiments, the finite element method is used to analyze the stress field of the 3D cracked microstructure, to optimize the sensing performance by tuning the nanoscale crack morphology. Finally, we propose the optimal design of sensor structure with controllable regular annular cracks on polymeric substrate according to a preferred embodiment which has regular cracks arranged in a staggered fashion along an incline plane as, for example, illustrated in FIGS. 2A and 2B.

To characterize the electrical performance of the TRACE sensor 304 according to an example embodiment, Au/Ti layers were deposited on a piece of ultra-flat glass substrate 314 as the electrodes e.g. 300, 308. When applying 0-20 kPa on the TRACE sensor 304 (strain rate: 5 μm/s), the registered resistance continuously and reversibly decreases from $10^8$ ohms to $10^3$ ohms as shown in curves 316, 317 in FIG. 3B. The sensor 304 exhibited high sensitivity and wide sensitive range when comparing with other piezo-resistive sensors [8]. A control of such a piezo-resistive sensor, i.e. PEDOT:PSS-coated micropyramidal sensor, was fabricated and compared, curves 318, 319 with the TRACE sensor, curves 316, 317. As can be seen from FIG. 3B, the TRACE sensor (curves 316, 317) demonstrated a much higher sensitivity and wider sensitive range as compared to the control sensor (curves 318, 319). Specifically, the control (curves 318, 319) shows a good sensitivity only under low loadings, with a rapid decline of sensitivity when the pressure applied exceeds 2 kPa. The TRACE sensor (curves 316, 317) also shows a low hysteresis (2.37%) in pressure response between loading and unloading. In contrast, the PEDOT: PSS-coated micropyramidal control sensor (curves 318, 319) shows a high hysteresis (79%). The low hysteresis of the TRACE sensor (curves 316, 317) advantageously enables a high accuracy of the sensor according to example embodiments.

Figure 4:
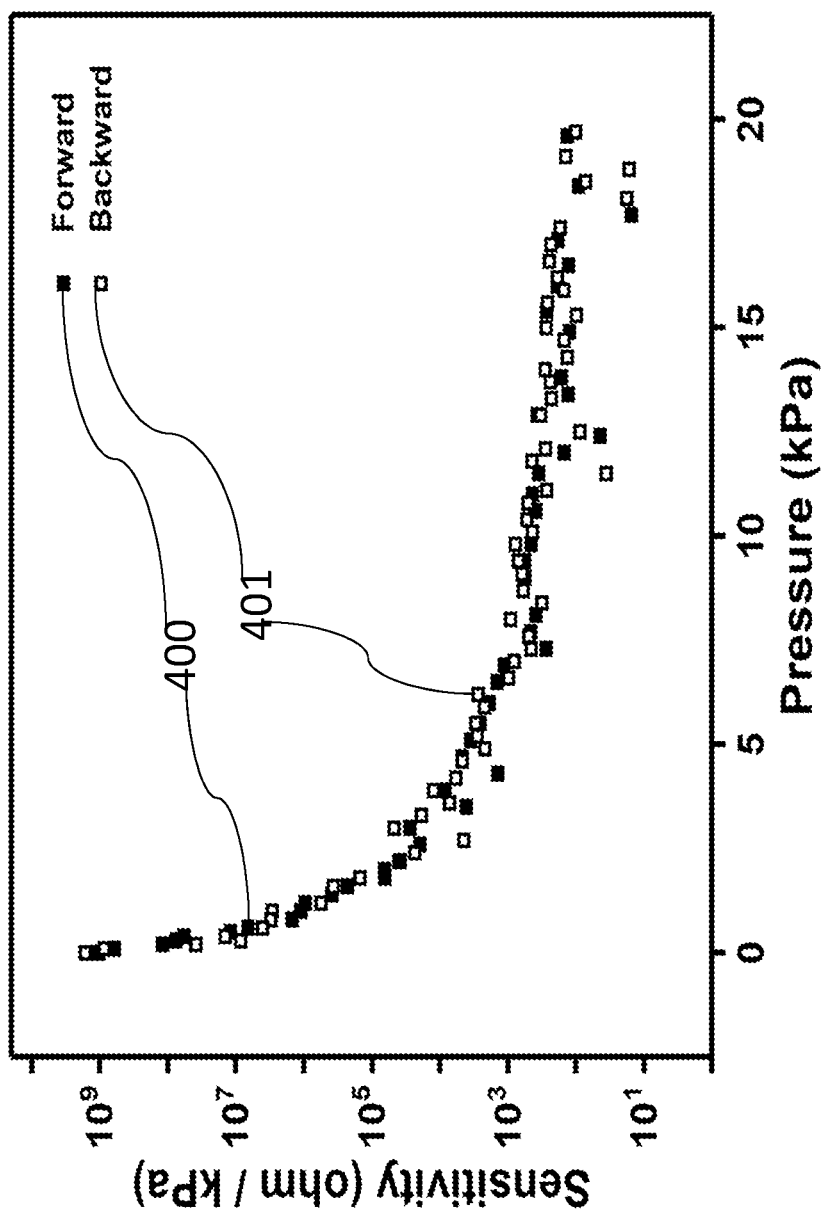
FIG. 4 shows a graph illustrating the pressure-induced sensitivity of a sensor according to an example embodiment.

Sensitivity of the pressure sensor 304 according to an example embodiment is computed from the differential of the pressure-resistance curves 316, 317, and the resulting forward and backward sensitivity curves 400, 401 are shown in FIG. 4. The sensor 304 has a high sensitivity of $10^9$ ohm/kPa. With 20 kPa of load applied, sensitivity remains reasonably high at $10^2$ ohm/kPa. The result indicates both high sensitivity and wide-sensitive range are advantageously achievable according to example embodiments. Loading (curve 400) and unloading (curve 401) showed comparable pressure induced sensitivity change. In addition, sensitivity at different loads remained consistent over several cycles.

Figure 5B:
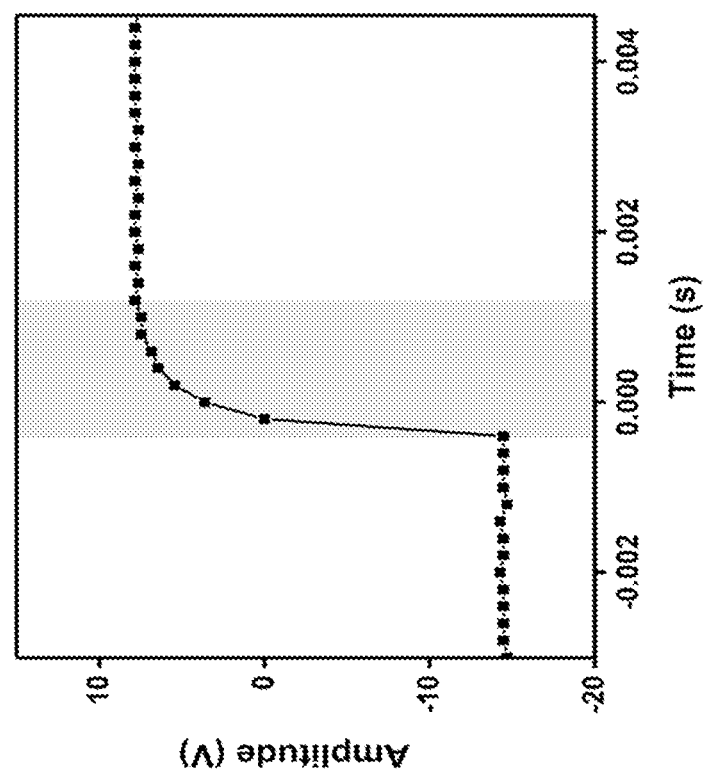
FIG. 5B shows a detail of the groan of FIG. 5A illustrating fast response time (1.4 ms) is exhibited when the pressure is applied on the sensor according to an example embodiment.
Figure 5A:
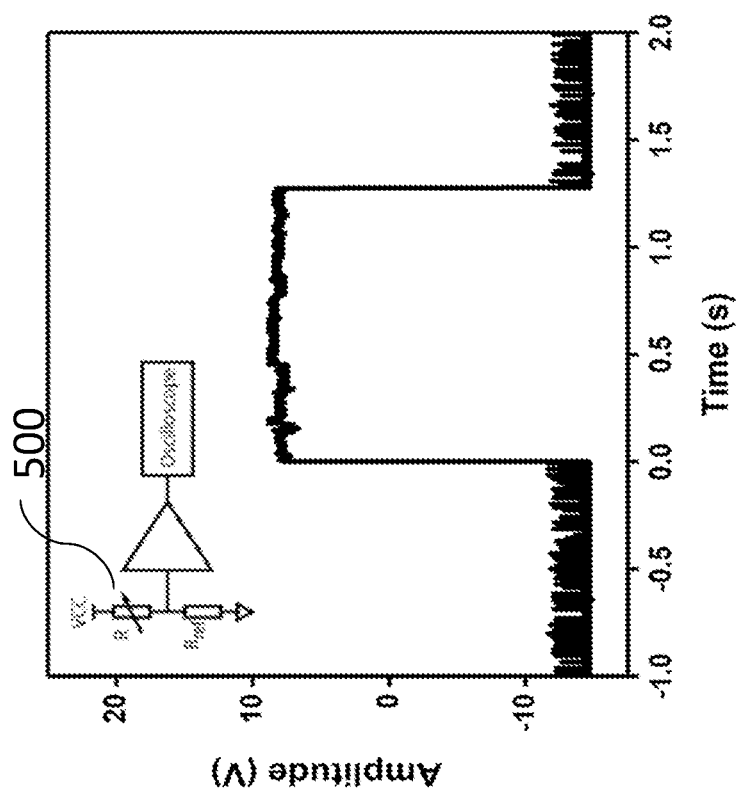
FIG. 5A shows a graph illustrating the result of the detection of a small pressure (15 Pa), using a sensor according to an example embodiments, together with a schematic of the circuit design.

FIGS. 5A and 5B, the latter being a zoomed portion of the former, show that a small pressure of 15 Pa can be detected by the TRACE sensor 500 according to an example embodiment. Upon applying the load, a fast response time of 1.4 ms is attained. It was found that the detection of smaller pressure was dependent on the split of cracks. Generally, it was found that a threshold force was applicable to make the split cracks sufficiently reconnected and form the conductive path. It was found that the resistance change is also contributed by the contact area increase of the metal film with the conductive electrodes compressing on the cracked metal film 3D structures.

Figure 6:
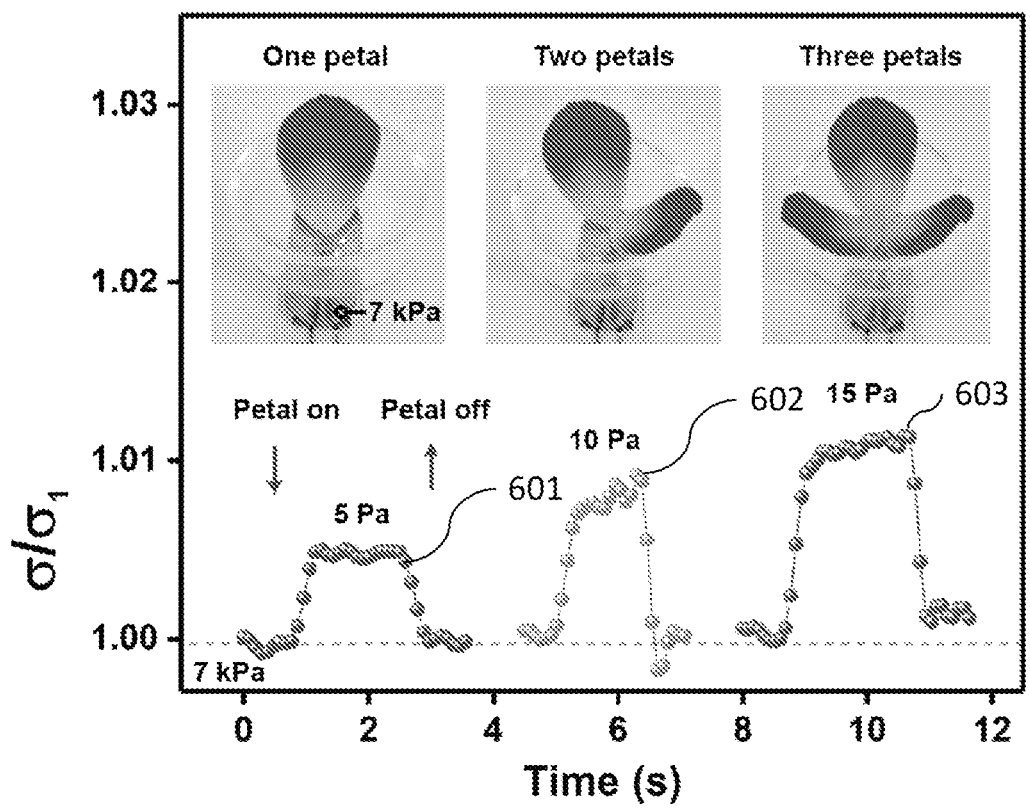
FIG. 6 shows illustrating the detection of small pressure (5 Pa, 10 Pa and 15 Pa) under a load of 7 kPa using a sensor according to an example embodiment, together with photographs showing the experimental set-up.

It was also found that the TRACE sensor according to an example embodiment can advantageously maintain its sensitivity even under a high load, i.e. it can detect small pressure even when a high load has already been applied. For example, with reference to FIG. 6, the small pressures of 5 Pa, 10 Pa and 15 Pa are detected by the TRACE sensor 600 according to an example embodiment under a load of 7 kPa by way of pre-loading, as shown in curves 601-603 in FIG. 6. This advantage is evidently superior when comparing with other pressure sensors that are sensitive only in low-load range.

Figure 7A:
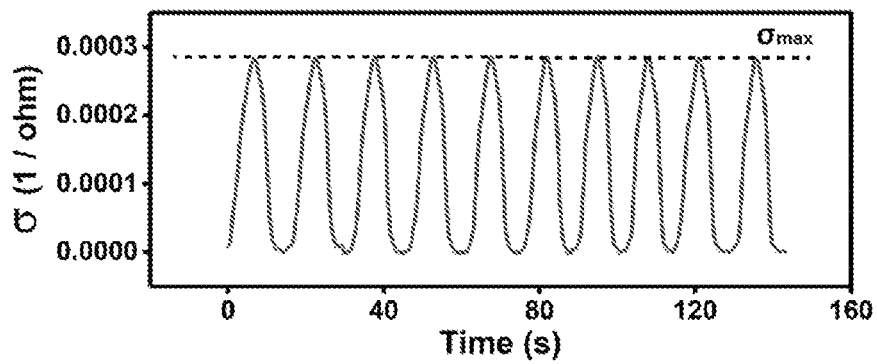
FIG. 7A shows a graph illustrating cyclic testing a sensor according to an example embodiments, specifically repeat of 10 cycles.
Figure 7B:
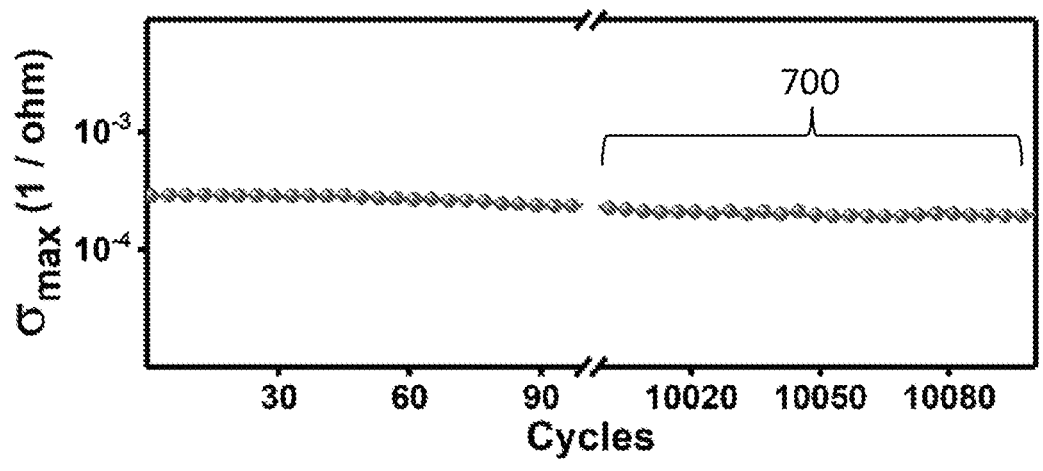
FIG. 7B shows a graph illustrating cyclic testing a sensor according to an example embodiments, specifically maximum conductivity change over 10,000 cycles.

The TRACE sensor according to an example embodiment was tested to about 10,000 compression and release cycles when pressure of 20 kPa was applied. With reference to FIGS. 7A and 7B, the sensor according to an example embodiment was tested with cyclic loads. Here, the conductance of the sensor is defined as σ (σ=1/R), which will increase with loads. When the pressure of 20 kPa was applied on the sensor at the specific strain rate (10 μm/s), σ was acquired to quantify the cyclic pressure response. $\sigma_{max}$ refers to the conductance when the load is 20 kPa. The TRACE sensor according to an example embodiment exhibited reversible behavior and comparable $\sigma_{max}$ over multiple cycles, see FIG. 7A. The $\sigma_{max}$ was further compared before and after 10,000 times of cyclic loads. Before 10,000 cycles of compression, the value remained stable and continuous over 100 cycles of measurement (compare FIG. 7A). After 10,000 cycles, $\sigma_{max}$ showed a slight decline but remained steady over another 100 cycles of measurement 700, see FIG. 7B. The slight decline is believed to be because of the crack propagation during cyclic loads, which has been discussed in previous research work [9]. It is believed that over sequential compression cycles, there will be some change in the crack configuration in example embodiments, and hence a preferred embodiment may have a less rigid conductor applied on the cracked metal film, e.g. conductive textiles/cloth.

Figure 8B:
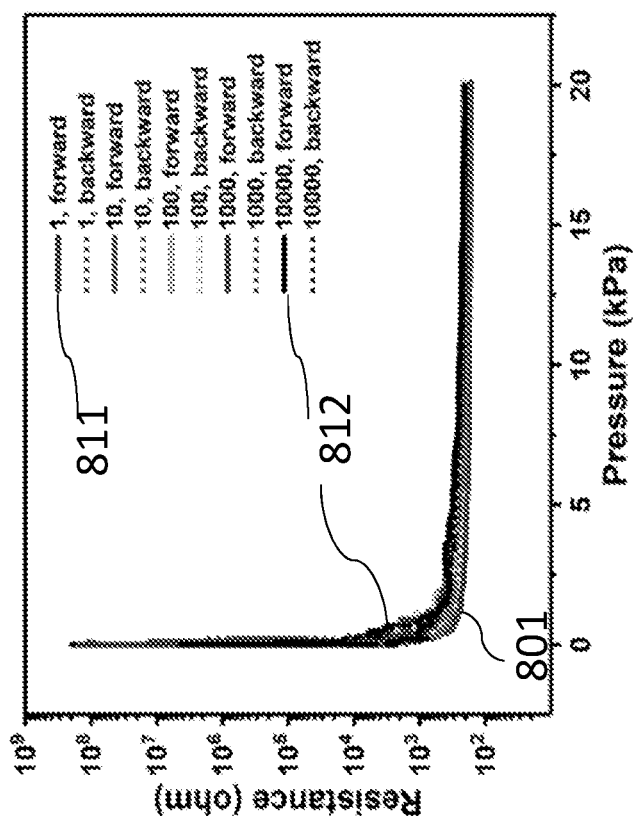
FIG. 8B shows a graph illustrating cyclic testing of a sensor according to an example embodiment with a flexible electrode, specifically pressure response of the sensor after 1, 10, 100, 1000 and 10000 cycles of compression.
Figure 8A:
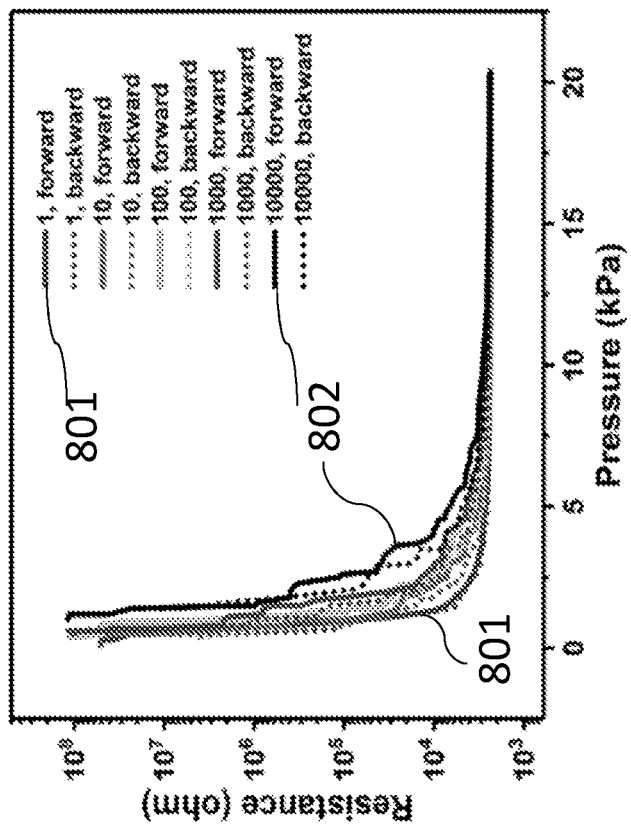
FIG. 8A shows a graph illustrating cyclic testing of a sensor according to an example embodiment with a rigid electrode, specifically pressure response of the sensor after 1, 10, 100, 1000 and 10000 cycles of compression.
Figure 9:
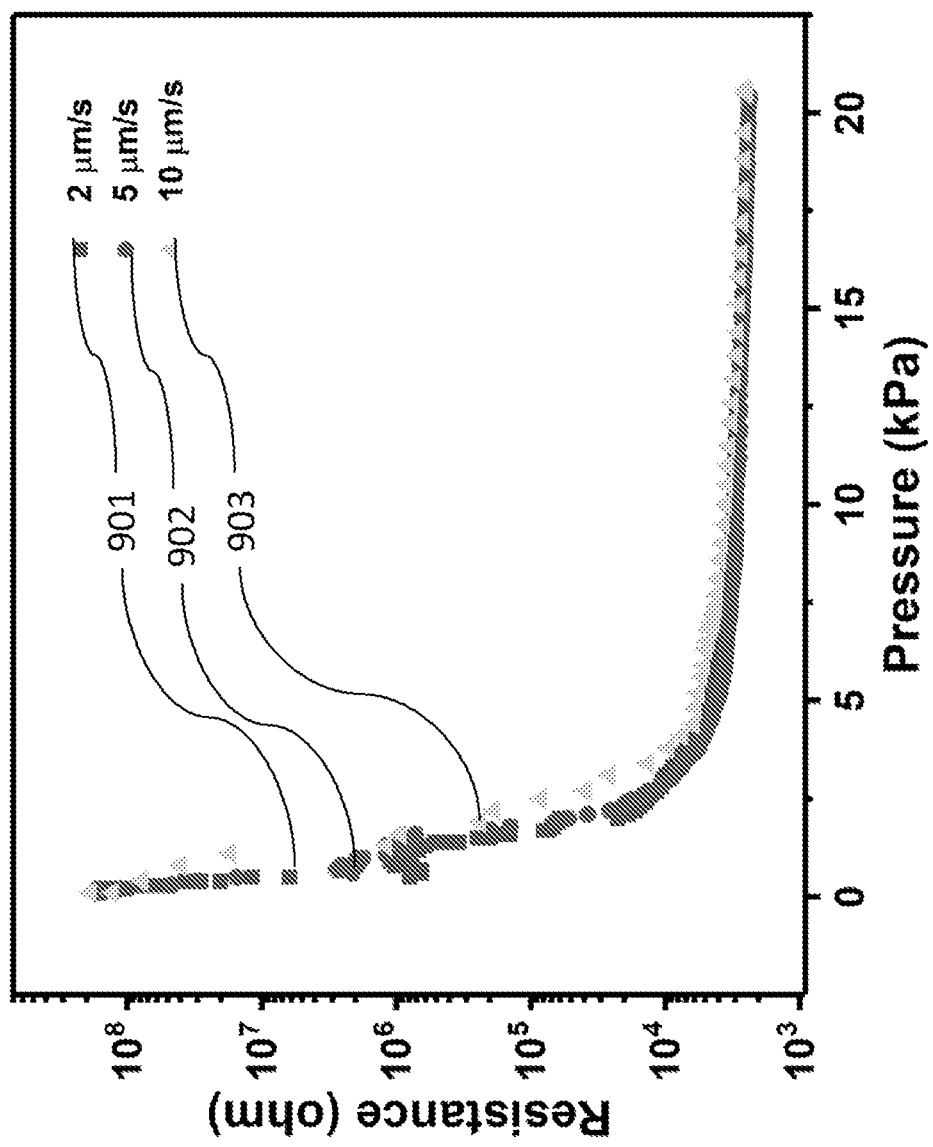
FIG. 9 shows a graph illustrating comparable pressure responses of a sensor according to an example embodiment under different compressive strain rates.

To study the crack propagation during cyclic loads, pressure responses of a TRACE sensor according to an example embodiment were measured up to 10,000 times of cyclic compression (see FIG. 8A). Under the same pressure, resistance increased during cyclic loads and the pressure response got to shift, compare e.g. curve 801, $1^{st}$ forward cycle, and curve 802, $10000^{th}$ forward cycle. This is believed to be induced by the crack propagation, during which the increasing number of cracks can be regarded as the increasing number of resistors in series connection. Besides the increase of resistance, propagated cracks are also believed to escalate the threshold force needed to form the conductive path. This could be observed from the pressure response of the TRACE sensor according to an example embodiment after 10,000 times of compression. To ameliorate the issue caused by crack propagation, flexible electrodes were present according to another example embodiment. Conductive cloth was selected as electrodes in this example embodiment. After cyclic loads on the sensor, the increase in resistance and the shift of pressure response got attenuated (compare e.g. curve 811, $1^{st}$ forward cycle, and curve 812, $10000^{th}$ forward cycle in FIG. 8B). This provides a promising solution for the development of a more reliable sensor based on metal cracks according to example embodiments. flexible electrodes can, for example, be fabricated by patterning conductive cloth, or depositing conductive polymer (e.g. CNTs, silver nanowires) or depositing thin metal film on polymeric substrates (e.g. PDMS, Ecoflex) according to example embodiments, noting that the flexible electrodes can also have a low flexural modulus similar to or less than the modulus of the sensor layer and metal layers. The TRACE sensor according to example embodiments advantageously displays a strain rate independent performance, which is an important characteristic of a pressure sensor. Specifically, when pressure was applied on the sensor at different strain rates (2 μm/s, 5 μm/s and 10 μm/s), consistent resistance versus pressure curves were attained, see curves 901-903 in FIG. 9.

Figure 10B:
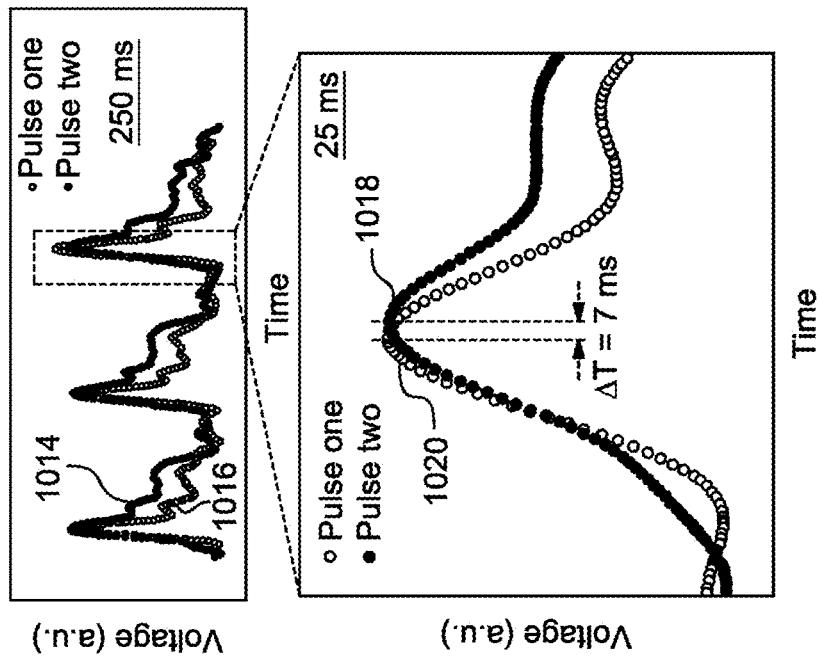
FIG. 10B shows a graph illustrating results of pulse tracing at radial artery using a sensor according to an example embodiment.
Figure 10A:
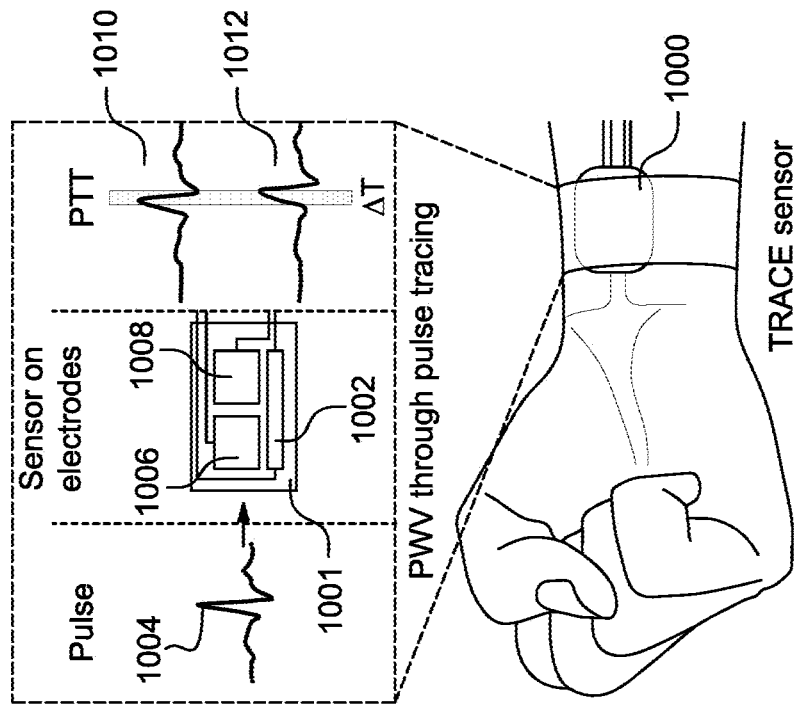
FIG. 10A shows schematic drawings illustrating localized pulse tracing and PWV measurement using a sensor according to an example embodiment, specifically a schematic of localized pulse tracing through multi-channel electrodes.
Figure 11:
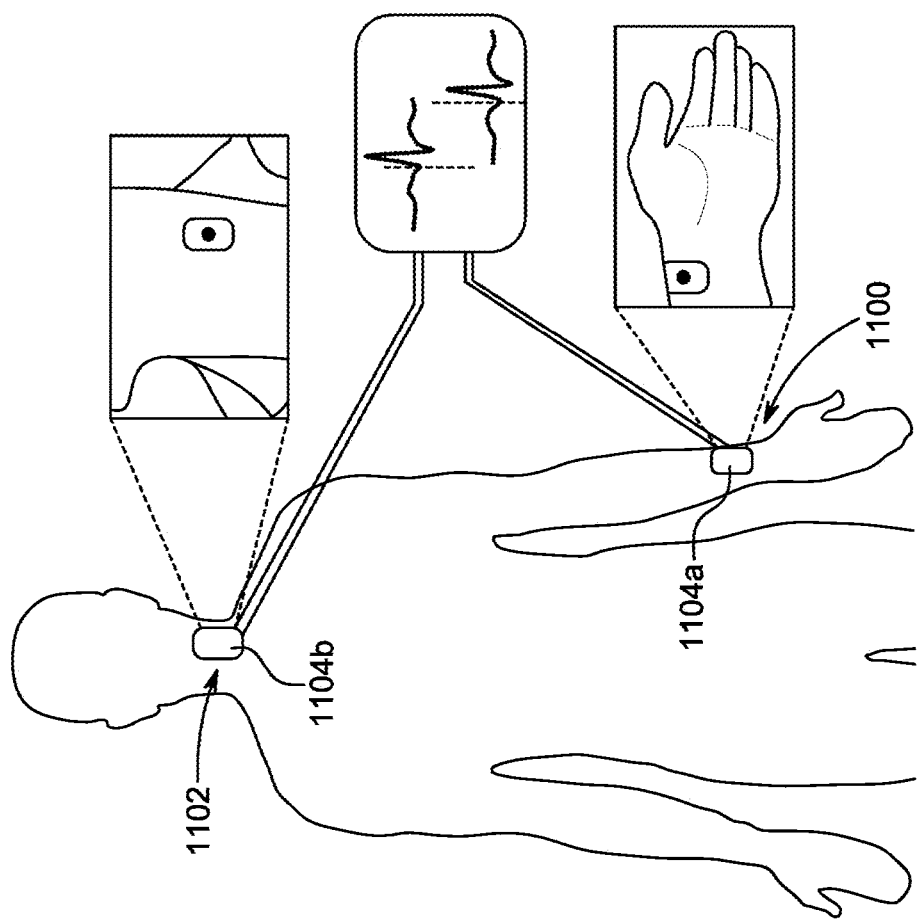
FIG. 11 shows a schematic drawing illustrating simultaneous pulse measurement at carotid artery and radial artery using sensors according to example embodiments.

Accordingly, the TRACE sensor according to example embodiments exhibits high sensitivity, wide-sensitive range and low hysteresis, indicating the good potential in the application of wearable devices, by way of example, not limitation. To demonstrate its feasibility in health monitoring, pulse measurement was carried out by designing the TRACE sensor 1000 according to an example embodiment on flexible electrodes. With reference to FIG. 10A, gold was deposited on PET 1001 as flexible electrodes e.g. 1002 and they were assembled with a micropatterned Pt layer/elastomer structure (compare 302 in FIG. 3A) to form a TRACE sensor according to an example embodiment. Pulse waves e.g. 1004 could be detected at radial artery, indicated at numeral 1100 in FIG. 11, and carotid artery, indicated at numeral 1102 in FIG. 11, simultaneously using two TRACE sensors 1104*a, b*.

Figure 12:
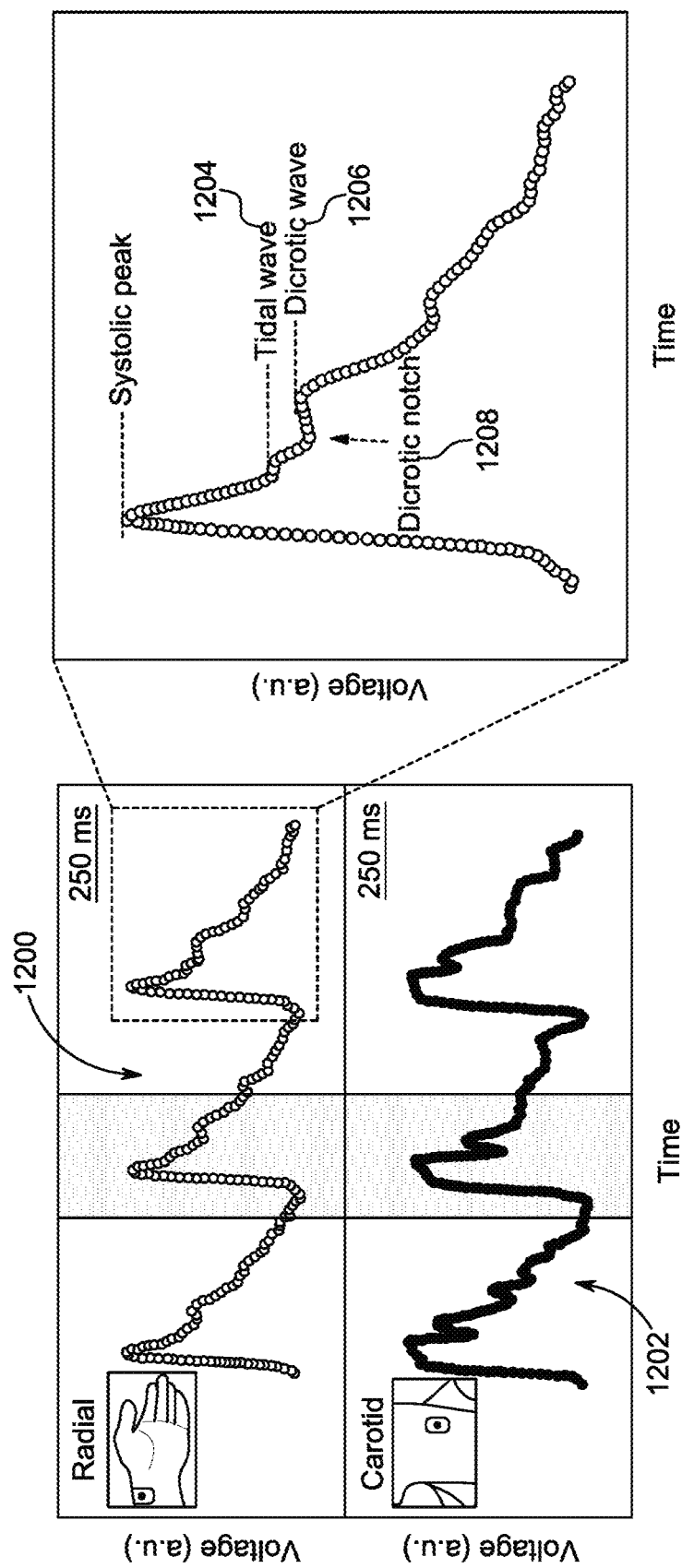
FIG. 12 shows graphs illustrating pulse measurement and tracing from carotid artery to radial artery using sensors according to example embodiments together with a zoom-in pulse wave at radial artery.

By tracing the pulse transit time (PTT) through pulses at these two sites 1100, 1102, the pulse wave velocity (PWV) can be acquired by dividing the distance by PTT (PWV=Distance/PTT). The distance refers to the length difference between heart-to-radial artery and heart-to-carotid artery (~75 cm). Pulse waves detected at radial artery and carotid artery are displayed in curves 1200 and 1202, respectively, in FIG. 12. Various waves e.g. 1204, 1206 and dicrotic notch 1208 of radial pulse could be clearly distinguished, which was attributed to the fast response time of the TRACE sensor according to an example embodiment. A PTT of 67 ms was traced through a foot-to-foot recognition of pulses and a PWV of ~11 m/s was acquired from carotid artery and radial artery.

Returning to FIG. 10A, for the first time measuring the localized PWV only at the radial artery was demonstrated, to the best of the inventors' knowledge, through the design of multi-channel electrodes in the TRACE sensor 1000 according to an example embodiment. Specifically, a first measurements channel extends between electrodes 1002 and 1006, and a second measurement channel extends between electrodes 1002 and 1008. When the pulse passes through the respective electrode pairs, distinct waves from the two different channels were attained and their time difference was recognized as ΔT between the PTT measurement pulses 1010 and 1012 from the respective channels, as shown in FIG. 10A. The overlaid detected pulse curves 1014, 1016 at the two sites of the radial artery are shown in FIG. 10B. The disparity of the configurations of these two pulses is attributed to the different amplitude and timing of reflected waves at the different sites. However, both pulse curves 1014 and 1016 exhibited a recognizable pulse peak, e.g. 1018, 1020. The PTT was obtained through a peak-to-peak as ~7 ms, and the localized PWV was acquired as ~0.6 m/s.

Benchmarking Sensor Hysteresis Versus Sensitivity for TRACE Sensors According to Example Embodiments:

Current sensors technology can be evaluated by having an index that incorporates both sensitivity and hysteresis.

Here, we introduce an index value, termed SpHe, which can be used to determine ratio of peak sensitivity (Sp) to electrical hysteresis (He) of a compressive type pressure sensor.

It is shown that a TRACE sensor according to an example embodiment can achieve the highest SpHe value compared to current published sensors. It is noted that many literature papers do not include hysteresis data. Here, a TRACE sensor according to an example embodiment is compared to publications with published hysteresis data available to the present inventors.

Benchmark Methodology for TRACE Sensors According to Example Embodiments:

1. Sensitivity

Figure 13:
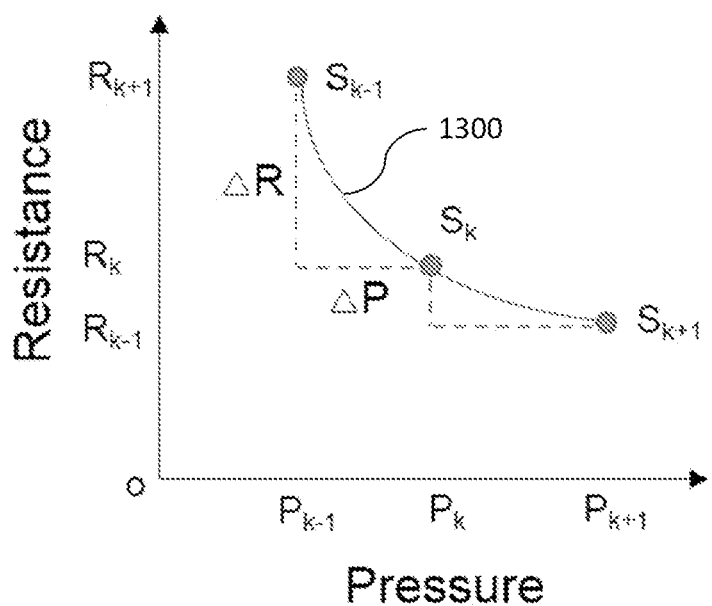
FIG. 13 shows a graph illustrating the numerical method of computing sensitivity in terms of resistance-pressure curve.
Figure 14:
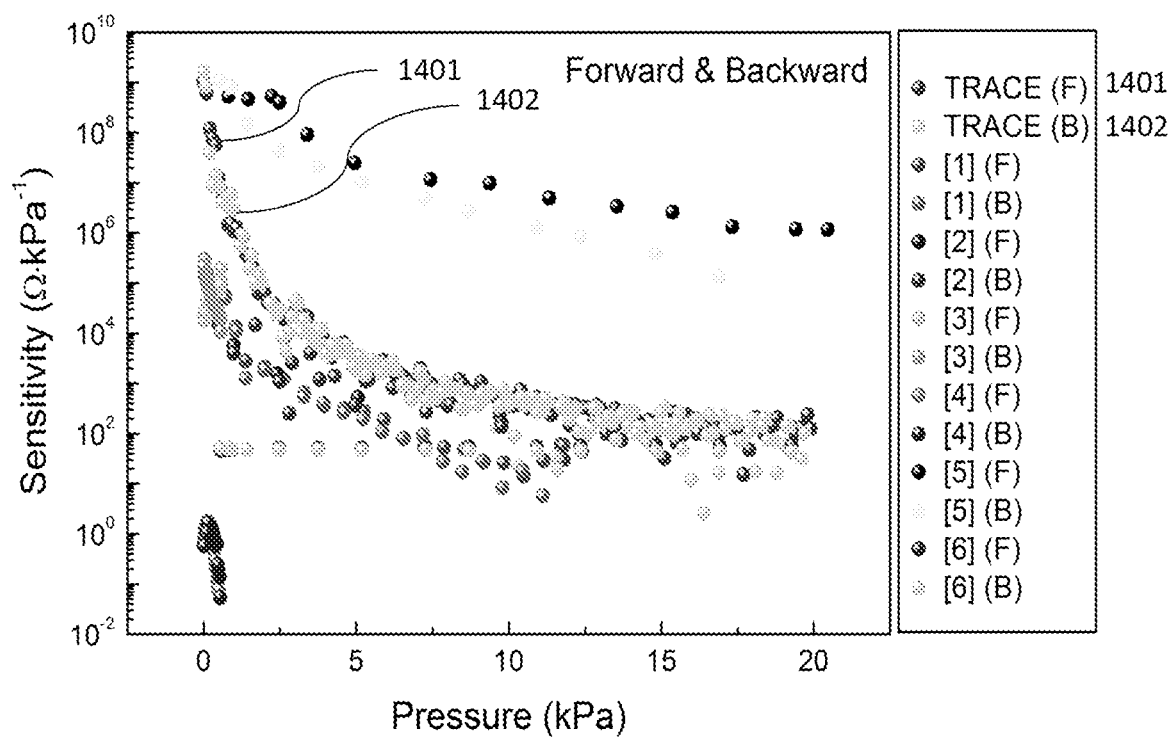
FIG. 14 shows a graph illustrating a comparison of sensitivity-pressure curve under loading/unloading of a sensor according to an example embodiment and existing sensors.
Figure 15:
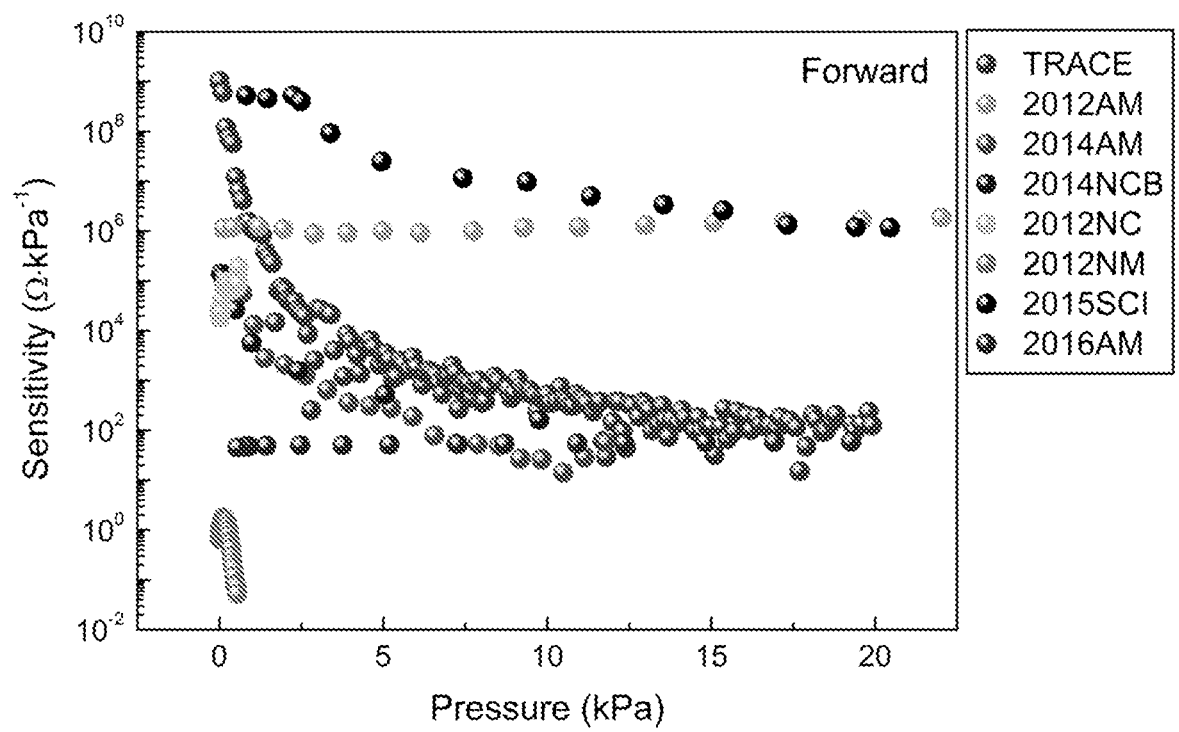
FIG. 15 shows a graph illustrating a comparison of sensitivity-pressure curve under loading path of a sensor according to an example embodiment and existing sensors.

In order to compare the sensitive property, one unifying computing methodology is presented here to evaluate piezoresistive pressure sensors in references. The original data of resistance/current and correspondent pressure was collected from scientific papers. Then, all data was transferred into the presented unified indicators and units, namely, resistance-pressure curve, where Ω for resistance and kPa for pressure. The definition of sensitivity is generally considered to be the change rate of resistance with the increasing pressure applied on sensors. In the benchmark methodology presented here, the numerical method such as centered difference formula was employed to obtain the sensitivity curve from the relation of resistance and pressure. The derivative at any one resistance data point was calculated by selecting the average of the slopes between that data point and its two neighbor data points. FIG. 13 illustrates the schematic of numerically calculating sensitivity from resistance-pressure curve 1300. The derivative function applied to discrete data points e.g. $S_k$ can be expressed as:

$$S_{F/B} = \frac{\partial R_{F/B}}{\partial P}\bigg|_{P_k} \tag{1}$$
$$= \frac{1}{2}\left(\frac{R_{k+1} - R_k}{P_{k+1} - P_k} + \frac{R_k - R_{k-1}}{P_k - P_{k-1}}\right)$$

where $S_F$, $S_B$ and $R_F$, $R_B$ denote forward and backward sensitivity and resistance, respectively, P is applied pressure, and $R_k$ is any one point of resistance. FIG. 14 and FIG. 15 show the sensitivity-pressure curves for loading/unloading and only forward loading conditions, respectively, of a TRACE sensor (curves 1401, 1402, 1501) according to an example embodiment as compared to published sensors.

2. Electromechanical Hysteresis

Figure 16:
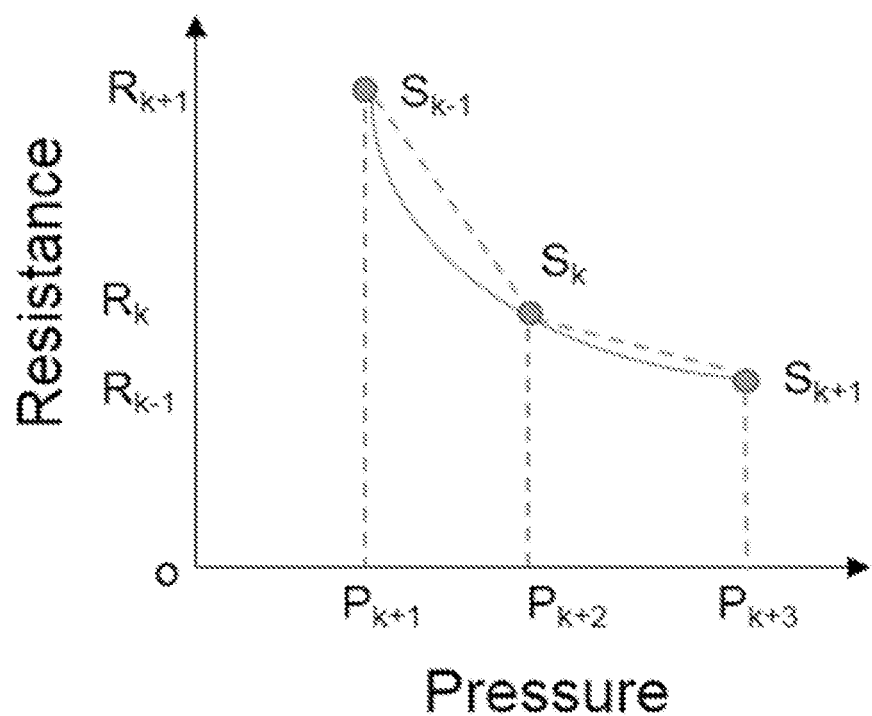
FIG. 16 shows a graph illustrating the numerical method of calculating electromechanical hysteresis.
Figure 17:
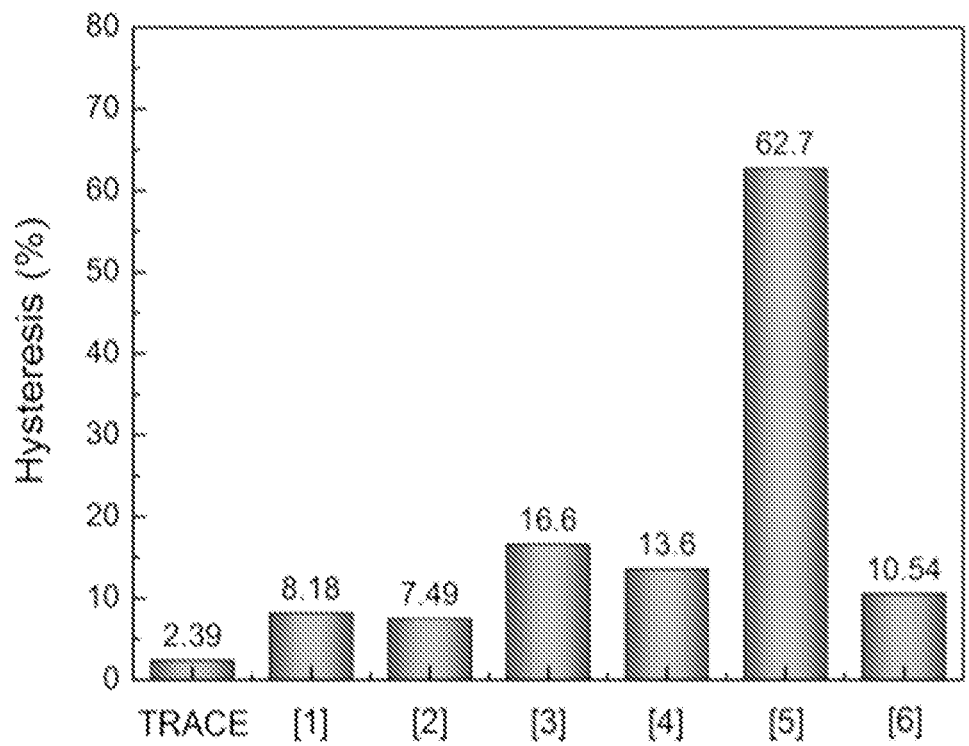
FIG. 17 shows a graph illustrating a comparison of electromechanical hysteresis under loading path of a sensor according to an example embodiment and existing sensors.

The electromechanical hysteresis is one critical factor of pressure sensors. First, the area difference between resistance-pressure curves of loading/unloading paths are calculated. Then the hysteresis is considered as the ratio of the area difference against loading curve. The hysteresis data is numerically calculated by trapezoid approximation integration method. FIG. 16 depicts the schematic of the algorithm for getting the hysteresis. The electromechanical [hysteresis indicating the ability to maintain electric performance after loading/unloading, is expressed as:

$$H = \left|\frac{\sum A_F - \sum A_B}{\sum A_F}\right| \times 100\% \tag{2}$$

and $$A_{F/B} = \sum_{k=1}^{n-1} \frac{1}{2}(P_{k+1} - P_k)[R_{F/B}(P_{k+1}) + R_{F/B}(P_k)] \tag{3}$$

where H is the indicator of electric hysteresis, $A_F$, $A_B$ denote integration area of resistance-pressure curve for forward and backward path, and P is pressure. FIG. 17 gives hysteresis data for various piezoresistive pressure sensors, including a TRACE sensor according to an example embodiment.

Figure 18:
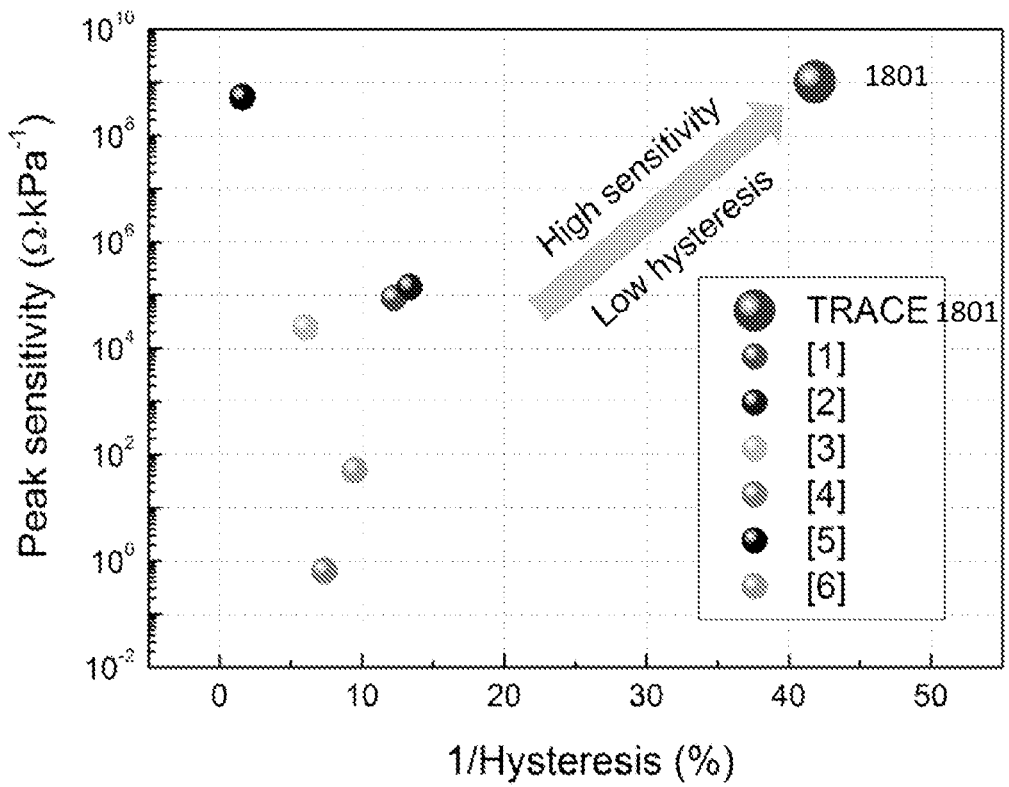
FIG. 18 shows a graph illustrating a comparison of peak Sensitivity and Hysteresis values of a sensor according to an example embodiment and existing sensors.

Benchmarking Results Using Index Value SpHe for TRACE Sensor According to an Example Embodiment:

FIG. 18 shows a plot of peak sensitivity and hysteresis values for current piezoresistive sensors compared to a TRACE sensor according to an example embodiment (data point 1801).

Figure 19:
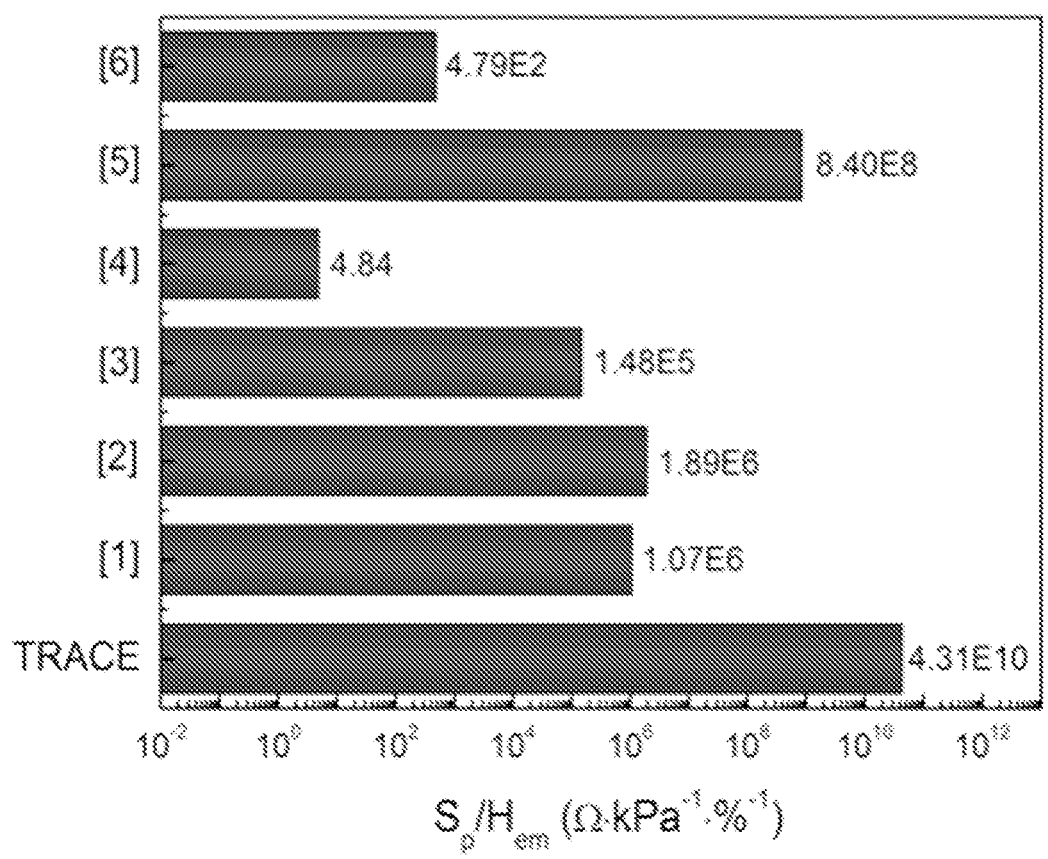
FIG. 19 shows a graph illustrating a comparison of SpHe value of a sensor according to an example embodiment and existing sensors.

FIG. 19 shows a plot of index value SpHe for current piezoresistive sensors compared to a TRACE sensor according to an example embodiment.

In one embodiment, there is provided a sensing structure for a compressive-type pressure sensor, the sensing structure comprising:

an elastic micropatterned substrate defining a plurality of 3-dimensional microstructures, each microstructure comprising a tip portion pointing away from the substrate in a first direction; and a conductive film on the elastic micropatterned substrate such that the 3-dimensional microstructures are substantially covered by the conductive film, wherein the conductive film comprises cracks in areas on 3-dimensional microstructures.

The cracks may comprise substantially annular cracks in areas on the 3-dimensional microstructures.

The conductive film may be free from cracks at the tip portions of the 3-dimensional microstructures.

The sensing structure may further comprise:

electrodes configured to be disposed on the conductive film covered tip portions of the 3-dimensional microstructures for measuring a resistance of a conductive path comprising portions of the conductive film in the areas on the 3-dimensional microstructures when a load is applied to the sensor for deforming the 3-dimensional microstructures.

The sensing structure may exhibit a ratio of peak sensitivity to electrical hysteresis of more than about 1E9 $\Omega Pa^{-1} \cdot \%^{-1}$.

The electrodes may be formed on an electrode substrate.

The electrodes may comprise flexible electrodes.

The flexible electrodes may be formed on a flexible electrode substrate.

In one embodiment, there is provided a compressive pressure sensor exhibiting a ratio of peak sensitivity to electrical hysteresis of more than about 1E9 $\Omega Pa^{-1} \cdot \%^{-1}$ FIG. 20 shows a flow-chart 2000 illustrating a method of fabricating a sensing structure for a compressive-type pressure sensor.

At step 2002, an elastic micropatterned substrate defining a plurality of 3-dimensional microstructures is provided, each microstructure comprising a tip portion pointing away from the substrate in a first direction. At step 2004, a conductive film is formed on the elastic micropatterned substrate such that the 3-dimensional microstructures are substantially covered by the conductive film. At step 2006, cracks are formed in the conductive film in areas on 3-dimensional microstructures.

Forming the cracks may comprise providing a rigid substrate on the conductive film covered 3-dimensional microstructures and applying a load to the 3-dimensional microstructures via the rigid substrate.

The method may comprise providing a soft cushioning material between the rigid substrate and the conductive film covered 3-dimensional microstructures during the applying of the load.

Forming the cracks may comprise forming substantially annular cracks in areas on the 3-dimensional microstructures.

Forming the cracks may comprise leaving the conductive film free from cracks at the tip portions of the 3-dimensional microstructures.

The method of may further comprise:

disposing electrodes on the conductive film covered tip portions of the 3-dimensional microstructures for measuring a resistance of a conductive path comprising portions of the conductive film in the areas on the 3-dimensional microstructures when a load is applied to the sensor for deforming the 3-dimensional microstructures.

The method may comprise forming the electrodes on an electrode substrate.

The electrodes may comprise flexible electrodes.

The method may comprise forming the flexible electrodes on a flexible electrode substrate.

Embodiments of the Present Invention can have One or More of the Following Features and Associated Benefits/Advantages:

| Feature | Benefit/Advantage |
| --- | --- |
| New method of fabricating pressure sensor, with controllable nanoscale crack morphology on microscale polymer | Harnessing 3D nanoscale crack to design novel pressure sensor structure with predictable and tunable sensing performance |
| High sensitivity and wide sensitive range | Excellent sensing performance compared with other pressure or strain sensor. It is capable of detecting small pressure, and the sensitivity remained even under a high load |
| Low hysteresis | Improved accuracy and controllability of pressure detection regardless of loading or unloading |
| Pulse tracing | TRACE sensor is able to detect the pulse from carotid artery and radial artery simultaneously and get the comparable pulse wave velocity (PWV) to the result attained from other measurements. It can also trace pulse only at radial artery with designed multi-channel flexible electrodes |

Applications of embodiments of the present invention include, but are not limited to:

A highly sensitive pressure sensor to detect small pressure under different loading conditions.

A multipurpose pulse analyser for pulse measurement and pulse tracing.

Aspects of the systems and methods described herein, such as, but not limited to, the electrical measurements and/or analysis, may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the system include: microcontrollers with memory (such as electronically erasable programmable read only memory (EEPROM)), embedded microprocessors, firmware, software, etc. Furthermore, aspects of the system may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

The above description of illustrated embodiments of the systems and methods is not intended to be exhaustive or to limit the systems and methods to the precise forms disclosed. While specific embodiments of, and examples for, the systems components and methods are described herein for illustrative purposes, various equivalent modifications are possible within the scope of the systems, components and methods, as those skilled in the relevant art will recognize. The teachings of the systems and methods provided herein can be applied to other processing systems and methods, not only for the systems and methods described above.

The elements and acts of the various embodiments described above can be combined to provide further embodiments. These and other changes can be made to the systems and methods in light of the above detailed description.

In general, in the following claims, the terms used should not be construed to limit the systems and methods to the specific embodiments disclosed in the specification and the claims, but should be construed to include all processing systems that operate under the claims. Accordingly, the systems and methods are not limited by the disclosure, but instead the scope of the systems and methods is to be determined entirely by the claims.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

REFERENCES

[1] Chwee-Lin Choong, . . . , Jong-Jin Park. Highly Stretchable Resistive Pressure Sensors Using a Conductive Elastomeric Composite on a Micropyramid Array. Advanced Materials. 2014.

[2] Lijia Pan, Alex Chortos, Guihua Yu, Yaqun Wang, Scott Isaacson, Ranulfo Allen, Yi Shi, Zhenan Bao. An ultra-sensitive resistive pressure sensor based on hollow-sphere microstructure induced elasticity in conducting polymer film. Nature Comms. 2014.

[3] Shu Gong, Willem Schwalb, Yongwei Wang, Yi Chen, Yue Tang Jye Si, Bijan Shirinzadeh, Wenlong Cheng. A wearable and highly sensitive pressure sensor with ultrathin gold nanowires. Nature Comms. 2014.

[4] Changhyun Pang, Gil-Yong Lee, Tae-il Kim, Sang Moon Kim, Hong Nam Kim, Sung-Hoon Ahn and Kahp-Yang Suh. A flexible and highly sensitive strain-gauge sensor using reversible interlocking of nanofibers. Nature Materials. 2012.

[5] Benjamin C.-K. Tee, Alex Chortos, Andre Berndt, Amanda Kim Nguyen, Ariane Tom, Allister McGuire, Ziliang Carter Lin, Kevin Tien, Won-Gyu Bae, Huiliang Wang, Ping Mei, Ho-Hsiu Chou, Bianxiao Cui, Karl Deisseroth, Tse Nga Ng, Zhenan Bao. A skin-inspired organic digital mechanoreceptor. Science. 2015.

[6] Ling Qiu, M. Bulut Coskun, Yue Tang, Jefferson Z. Liu, Tuncay Alan, Jie Ding, Van-Tan Truong, and Dan Li* Ultrafast Dynamic Piezoresistive Response of Graphene Based Cellular Elastomers. Advanced Materials. 2016.

[7] Kang, D. et al. Ultrasensitive mechanical crack-based sensor inspired by the spider sensory system. Nature 516, 222-226 (2014).

[8] Choong, C. L. et al. Highly stretchable resistive pressure sensors using a conductive elastomeric composite on a micropyramid array. Adv. Mater. (2014). doi:10.1002/adma.201305182

[9] Park, B. et al. Dramatically Enhanced Mechanosensitivity and Signal-to-Noise Ratio of Nanoscale Crack-Based Sensors: Effect of Crack Depth. Adv. Mater. 28, 8130-8137 (2016).

The invention claimed is:

1. A sensing structure for a compressive-type pressure sensor, the sensing structure comprising:
   an elastic micropatterned substrate defining a plurality of 3-dimensional microstructures, each microstructure comprising a tip portion pointing away from the substrate in a first direction; and
   a conductive film on the elastic micropatterned substrate such that the 3-dimensional microstructures are substantially covered by the conductive film, wherein the conductive film comprises cracks in areas on 3-dimensional microstructures;
   wherein the conductive film is free from cracks at the tip portions of the 3-dimensional microstructures.

2. The sensing structure of claim 1, wherein the cracks comprise substantially annular cracks in areas around the 3-dimensional microstructures that are displaced from the tip portions.

3. The sensing structure of claim 2, wherein the 3-dimensional microstructures are in the form of micropyramids.

4. The sensing structure of claim 1, further comprising: electrodes configured to be disposed on the conductive film covered tip portions of the 3-dimensional microstructures for measuring a resistance of a conductive path comprising portions of the conductive film in the areas on the 3-dimensional microstructures when a load is applied to the sensor for deforming the 3-dimensional microstructures in a second direction substantially opposite to the first direction.

5. The sensing structure of claim 4, exhibiting a ratio of a highest sensitivity of the sensing structure, the sensitivity being a change rate of resistance in $\Omega$ with increasing pressure in kPa applied on the sensor structure, to electrical hysteresis, expressed as:

$$H = \left|\frac{\sum A_F - \sum A_B}{\sum A_F}\right| \times 100\%$$

where $$A_{FIB} = \sum_{k=1}^{n-1} \frac{1}{2}(P_{k+1} - P_k)[R_{FIB}(P_{k+1}) + R_{FIB}(P_k)]$$

and where:
   H is an indicator of electric hysteresis, in %, $A_F$,
   $A_B$ are integration areas of a resistance-pressure curve of the sensing structure for forward and backward path, respectively, and
   P is pressure on kPa.

6. The sensing structure of claim 4, wherein the electrodes are formed on an electrode substrate.

7. The sensing structure of claim 4, wherein the electrodes comprise flexible electrodes.

8. The sensing structure of claim 7, wherein the flexible electrodes are formed on a flexible electrode substrate.

9. A method of fabricating the sensing structure for the compressive-type pressure sensor of claim 1, the method comprising the steps of:
   providing the elastic micropatterned substrate defining the plurality of 3-dimensional microstructures, each microstructure comprising the tip portion pointing away from the substrate in a first direction;
   forming the conductive film on the elastic micropatterned substrate such that the 3-dimensional microstructures are substantially covered by the conductive film; and forming the cracks in the conductive film in areas on 3-dimensional microstructures;

wherein forming the cracks comprises leaving the conductive film free from cracks at the tip portions of the 3-dimensional microstructures.

10. The method of claim 9, wherein forming the cracks comprises providing a rigid substrate on the conductive film covered 3-dimensional microstructures and applying a load to the 3-dimensional microstructures via the rigid substrate.

11. The method of claim 9, comprising providing a soft cushioning material between the rigid substrate and the conductive film covered 3-dimensional microstructures during the applying of the load.

12. The method of claim 9, wherein forming the cracks comprises forming substantially annular cracks in areas on the 3-dimensional microstructures.

13. The method of claim 9, further comprising:

disposing electrodes on the conductive film covered tip portions of the 3-dimensional microstructures for measuring a resistance of a conductive path comprising portions of the conductive film in the areas on the 3-dimensional microstructures when a load is applied to the sensor for deforming the 3-dimensional microstructures in a second direction substantially opposite to the first direction.

14. The method of claim 13, comprising forming the electrodes on an electrode substrate.

15. The method of claim 13, wherein the electrodes comprise flexible electrodes.

16. The method of claim 15, comprising forming the flexible electrodes on a flexible electrode substrate.

17. The sensing structure of claim 1, wherein the 3-dimensional microstructures are in the form of micropyramids.

* * * * *